United States Patent
Kapec et al.

(10) Patent No.: US 11,819,396 B2
(45) Date of Patent: Nov. 21, 2023

(54) TAMPON AND TAMPON APPLICATION WRAPPER

(71) Applicant: Edgewell Personal Care Brands, LLC, Chesterfield, MO (US)

(72) Inventors: Jeffrey Kapec, Westport, CT (US); Yukiko Naoi, New York, NY (US); Pankaj Nigam, Ridgeweood, NJ (US); Adebimpe Ogunade, Saddle Brook, NJ (US)

(73) Assignee: EDGEWELL PERSONAL CARE BRANDS, LLC, Chesterfield, MO (US)

( * ) Notice: Subject to any disclaimer, the term of this patent is extended or adjusted under 35 U.S.C. 154(b) by 666 days.

(21) Appl. No.: 16/939,439

(22) Filed: Jul. 27, 2020

(65) Prior Publication Data

US 2020/0360200 A1   Nov. 19, 2020

Related U.S. Application Data

(63) Continuation of application No. 15/560,659, filed as application No. PCT/US2015/059695 on Nov. 9, 2015, now Pat. No. 10,758,432.
(Continued)

(51) Int. Cl.
*A61F 13/551* (2006.01)
*A61F 13/84* (2006.01)

(52) U.S. Cl.
CPC .... *A61F 13/55175* (2013.01); *A61F 13/5516* (2013.01); *A61F 13/5518* (2013.01);
(Continued)

(58) Field of Classification Search
CPC ............ A61F 13/55165; A61F 13/5517; A61F 13/55175; A61F 13/55185;
(Continued)

(56) References Cited

U.S. PATENT DOCUMENTS 3,058,469 A   10/1962   Crockford
3,123,210 A   3/1964   Hermanson et al.
(Continued)

FOREIGN PATENT DOCUMENTS

EP   0047747 A2   11/1982
JP   2004-97251 A   4/2004
(Continued)

OTHER PUBLICATIONS

International Preliminary Report on Patentability issued in connection with corresponding PCT Application No. PCT/US2015/059695 dated May 16, 2017.
(Continued)

*Primary Examiner* — Susan S Su

(57) ABSTRACT

A feminine hygiene product wrapper, comprising a front panel having a closed side lengthwise edge, an open side lengthwise edge, a bottom widthwise edge, and a top widthwise edge; a back panel having a closed side lengthwise edge, an open side lengthwise edge, a bottom widthwise edge, and a top widthwise edge; and an expandable side panel having a lengthwise extending first side edge, a lengthwise extending second side edge, a top edge, and a bottom edge, wherein the lengthwise extending first side edge is attached to the open side lengthwise edge of the front panel, and the lengthwise extending second side edge is attached to the open side lengthwise edge of the back panel.

13 Claims, 5 Drawing Sheets

Related U.S. Application Data

(60) Provisional application No. 62/077,413, filed on Nov. 10, 2014.

(52) U.S. Cl.
  CPC .... *A61F 13/84* (2013.01); *A61F 2013/55195* (2013.01); *A61F 2013/8497* (2013.01)

(58) Field of Classification Search
  CPC .......... A61F 2013/8497; A61F 13/5516; A61F 13/5518; A61F 13/84; A61F 2013/55195
  See application file for complete search history.

(56) References Cited

U.S. PATENT DOCUMENTS

| | | |
|---|---|---|
| 3,230,956 A | 1/1966 | Kargul |
| 4,182,336 A | 1/1980 | Black |
| 4,605,403 A | 8/1986 | Tucker |
| 4,692,162 A | 9/1987 | Binker et al. |
| 6,131,736 A | 10/2000 | Farris et al. |
| 6,203,512 B1 | 3/2001 | Farris et al. |
| 6,478,763 B1 | 11/2002 | Simonsen et al. |
| 6,913,146 B2 | 7/2005 | Bechyne et al. |
| 6,994,696 B2 | 2/2006 | Suga |
| 7,178,671 B2 | 2/2007 | Nichols et al. |
| 7,422,105 B2 | 9/2008 | Loyd et al. |
| 8,282,280 B2 | 10/2012 | Germanow et al. |
| 8,403,903 B2 | 3/2013 | Clark, Jr. et al. |
| 9,186,284 B1 | 11/2015 | Hernandez |
| 10,022,281 B1 | 7/2018 | Ramsey |
| 2003/0073970 A1 | 4/2003 | Suga |
| 2003/0116462 A1 | 6/2003 | Sorebo et al. |
| 2003/0120241 A1 | 6/2003 | Sorebo et al. |
| 2003/0220625 A1 | 11/2003 | Domeier et al. |
| 2004/0112779 A1 | 6/2004 | Arndt |
| 2004/0178104 A1 | 9/2004 | Mizutani et al. |
| 2005/0098466 A1 | 5/2005 | Thomas |
| 2005/0154365 A1 | 7/2005 | Zander et al. |
| 2006/0212015 A1 | 9/2006 | Peele |
| 2007/0151885 A1 | 7/2007 | Loyd et al. |
| 2008/0097364 A1 | 4/2008 | Yang |
| 2010/0042064 A1 | 2/2010 | Kondo et al. |
| 2010/0078348 A1 | 4/2010 | Kondo et al. |
| 2010/0094238 A1 | 4/2010 | Scarano |
| 2010/0121299 A1 | 5/2010 | Cooper |
| 2010/0298797 A1 | 11/2010 | Ehlenbach et al. |
| 2012/0024735 A1 | 2/2012 | Francis et al. |
| 2012/0283680 A1 | 11/2012 | Zander et al. |
| 2012/0310201 A1 | 12/2012 | Oates |
| 2013/0165887 A1 | 6/2013 | Eric et al. |
| 2013/0190711 A1 | 7/2013 | Hashino et al. |
| 2014/0276351 A1 | 9/2014 | Drewnowski et al. |
| 2015/0112294 A1 | 4/2015 | Dahl et al. |
| 2015/0305950 A1 | 10/2015 | Cousineau et al. |
| 2016/0167860 A1 | 6/2016 | Tomsovic et al. |
| 2017/0027772 A1 | 2/2017 | Agee |
| 2017/0319408 A1 | 11/2017 | Jackson |
| 2018/0318152 A1 | 11/2018 | Garcia |

FOREIGN PATENT DOCUMENTS

| | | |
|---|---|---|
| JP | 2007-54087 A | 3/2007 |
| WO | 03/082174 A1 | 10/2003 |
| WO | 2007078535 A1 | 7/2007 |

OTHER PUBLICATIONS

Search Report & Written Opinion issued in connection with corresponding PCT Application No. PCT/US2015/059695 dated Feb. 16, 2016.

Final Office Action issued in connection with U.S. Appl. No. 15/560,659 dated Feb. 12, 2020.

Non-Final Office Action issued in connection with U.S. Appl. No. 15/560,659 dated Sep. 18, 2019.

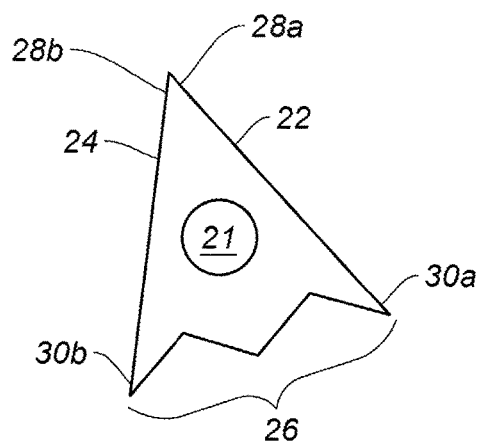
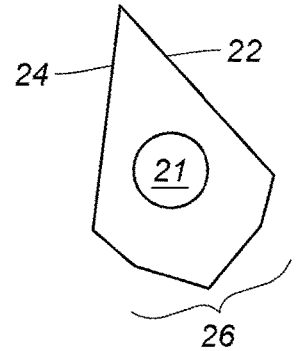
FIG. 11  FIG. 12
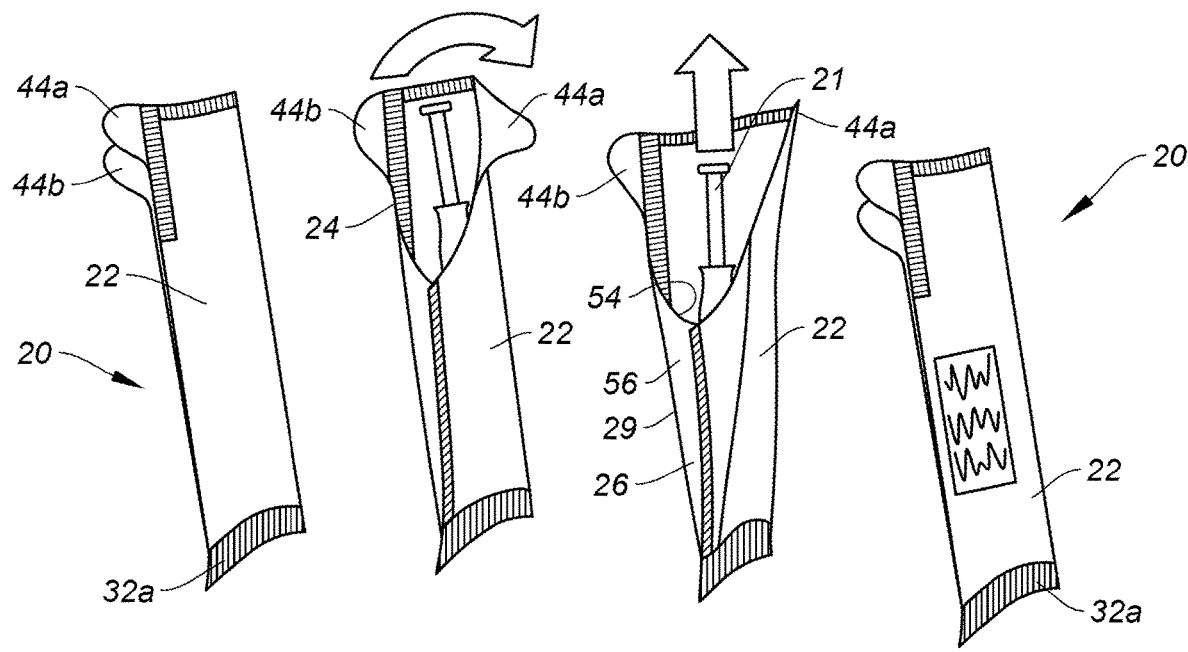
FIG. 13A  FIG. 13B  FIG. 13C  FIG. 13D

TAMPON AND TAMPON APPLICATION WRAPPER

CROSS-REFERENCE TO RELATED APPLICATIONS

This application is a continuation of U.S. application Ser. No. 15/560,659, filed on Sep. 22, 2017 which is a 371 International application of PCT/US2015/059695, filed on Nov. 9, 2015, which claims the benefit of priority to U.S. Provisional Patent Application Ser. No. 62/077,413 filed on Nov. 10, 2014 the contents of which are incorporated by reference herein.

BACKGROUND OF THE INVENTION

1. Technical Field

The present disclosure relates to tampons and tampon applicators in general and to containers for tampons and tampon applicators in particular.

2. Background Information

Feminine hygiene products, such as tampons, are typically packaged within a wrapper to keep the product hygienic prior to use. In many instances, the wrapper is also used to contain a used product prior to disposal. Prior art wrappers are typically made of a plastic film, such as polypropylene and polyethylene or other materials such as nonwovens, and paper, and laminates, to enclose the product completely. In some instances, it is not easy for a user to identify where or how the wrapper is intended to be opened. In such instances, the user may tear or otherwise open the wrapper in a manner that provides access to the unused product, but a lack of opening mechanism(s) and/or opening queues can prompt improper opening (e.g., tearing at the wrong point, or completely opening the package), which makes it difficult or impossible to use the same wrapper to thereafter effectively contain a used product. Even when some prior art wrappers are opened as intended, it can be difficult for the user to remove the product and more difficult to insert a used product in the wrapper because the opening is small relative to the size of the product. For example, it is not uncommon for a user to open a wrapper to remove the product and then subsequently have to expand a restrictive size opening to facilitate disposal of the used product within the wrapper.

Disposal of a used product into some prior art wrappers can also be difficult because a wrapper may not have sufficient integrity after being torn open to contain a used product. In those instances, a user may be forced to dispose of the wrapper and the used product separately which is wasteful (e.g. the user may elect to wrap the used product in toilet paper). Another problem users may experience relates to how the used product may be disposed of discreetly and effectively. For example, if a user has to change a product in a restroom that does not have an available disposal bin, or if the user is not comfortable with leaving a used product in the restroom, the user may elect to wrap the used product in toilet paper if the wrapper cannot be used, which provides a non-discreet and potentially unsanitary package for the user to carry away from the washroom.

Another deficiency of the prior art is the aesthetics of the wrapper. Some wrappers are overly plain in an attempt to provide a product that is discreet. Other wrappers are bright with decorative patterns in an attempt to attract youthful customers and/or to create enthusiasm at a delicate time for the consumer. Currently wrapped feminine care articles such as tampons fail to provide both a discreet product in a prior-to-use state (e.g., prior to opening) and also a positive, upbeat product during use (e.g., upon opening, during use, and optionally during disposal).

Some prior art products come with a bag that can be used for the disposal of used products. Such bags typically require an additional step in the changing process and require an item (i.e. the bag) in addition to the tampon be carried to the bathroom discreetly, which makes the changing process more cumbersome and less convenient for the user.

Yet another deficiency of the prior art is the amount of opening and/or space that is provided to the consumer upon opening the product, removing the product, and optionally returning a soiled product within the wrapper for disposal. Current tampon wrappers fail to achieve a small initial footprint that can be easily carried and is also discreet, while also providing an expanded state that enables the consumer to more easily remove the product from the wrapper and optionally place a soiled product within the wrapper for discreet disposal.

DISCLOSURE OF THE INVENTION

According to an aspect of the present disclosure, a feminine hygiene product wrapper with an exterior surface and an interior surface opposite thereto, the wrapper having a front panel, a back panel, and an expandable side panel. The front panel has a closed side lengthwise edge, an open side lengthwise edge, a bottom widthwise edge, and a top widthwise edge. The back panel has a closed side lengthwise edge, an open side lengthwise edge, a bottom widthwise edge, and a top widthwise edge. The expandable side panel has a lengthwise extending first side edge, a lengthwise extending second side edge, a top edge, and a bottom edge. The lengthwise extending first side edge is attached to the open side lengthwise edge of the front panel, and the lengthwise extending second side edge is attached to the open side lengthwise edge of the back panel.

According to another aspect of the present disclosure, a feminine hygiene product wrapper is provided that includes a panel and an expandable side panel. The panel includes a pair of lengthwise edges, a bottom widthwise edge, a top widthwise edge, an interior surface and an exterior surface. The expandable side panel extends between the lengthwise edges of the panel. The side panel has an interior surface, an exterior surface, and a top widthwise edge. The wrapper is closed along the bottom widthwise edge of the panel. The interior surfaces of the panel and the expandable side panel form an interior cavity operable to hold a feminine hygiene product. The wrapper is selectively configurable in a new product configuration wherein the interior cavity is closed adjacent the top widthwise edge of the panel, and an open configuration wherein the expandable side panel is at least partially expanded and the interior cavity of the wrapper is open.

In any of the aspects above, the expandable side panel may include one or more folds, which folds are oriented such that in the new product configuration a widthwise cross-sectional area of the wrapper is substantially uniform along the length of the wrapper, and in the open configuration the widthwise cross-sectional area of the wrapper adjacent the top widthwise edge is substantially larger than the widthwise cross-sectional area of the interior cavity adjacent the bottom widthwise edge.

The features and advantages of the present invention will become apparent in light of the detailed description of the invention provided below, and as illustrated in the accompanying drawings.

BRIEF DESCRIPTION OF THE DRAWINGS

The present disclosure is illustrated by way of example and not limited in the accompanying figures in which like reference numerals indicate similar elements.

FIG. 11 is a diagrammatic sectional view of the present wrapper in an open configuration proximate the bottom edge of the wrapper, at line 11-11 of FIG. 8.

FIG. 12 is a diagrammatic sectional view of the present wrapper in an open configuration, illustrating the expandable side panel deflected outwardly.

FIGS. 13A-13D diagrammatically illustrates the present wrapper in the new product configuration, and then the progressively to the right, the wrapper in the open configuration, then the product being removed, and then finally the wrapper in a closed configuration with a used product disposed in the interior cavity of the wrapper.

DETAILED DESCRIPTION

Figure 1:
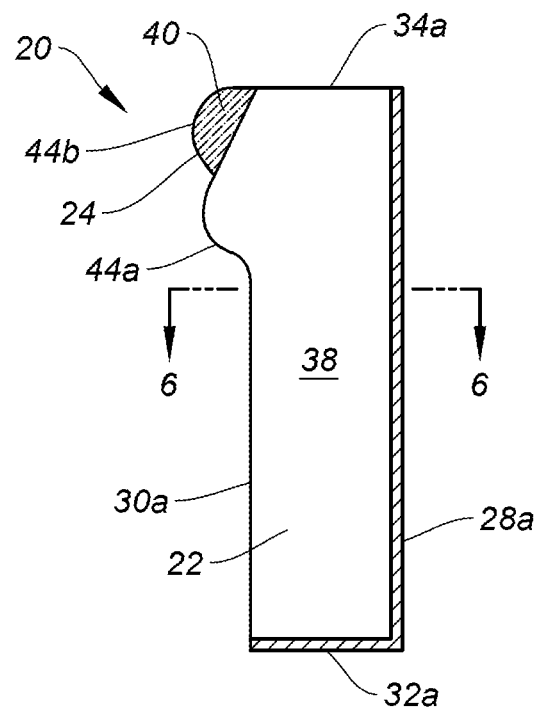
FIG. 1 is a diagrammatic planar view of the present wrapper (front panel side) in a new product configuration.

It is noted that various connections are set forth between elements in the following description and in the drawings (the contents of which are included in this disclosure by way of reference). It is noted that these connections are general and, unless specified otherwise, may be direct or indirect and that this specification is not intended to be limiting in this respect. A coupling between two or more entities may refer to a direct connection or an indirect connection. An indirect connection may incorporate one or more intervening entities.

Now referring to FIGS. 1-4, an embodiment of the present disclosure wrapper 20 for a feminine hygiene product 21 (e.g. a tampon or napkin product). The wrapper 20 has an exterior surface 23 and an interior surface 60 opposite thereto (i.e. the interior surface 60 is adjacent the product 21 contained within the wrapper 20). The wrapper 20 includes a front panel 22, a back panel 24, and an expandable side panel 26. The wrapper 20 is configurable in a new product configuration (e.g. see FIGS. 1 and 2), an open configuration (e.g. see FIGS. 4 and 8), and a closed used product configuration (e.g. see FIG. 13). In some embodiments, as will be described below, the wrapper 20 may also be configured in a folded used product configuration (e.g. see FIG. 14).

The front panel 22 may be described as having a closed side lengthwise edge 28a, an open side lengthwise edge 30a, a bottom widthwise edge 32a, and a top widthwise edge 34a. The back panel 24 may be described as having a closed side lengthwise edge 28b, an open side lengthwise edge 30b, a bottom widthwise edge 32b, and a top widthwise edge 34b. To facilitate the present description, the length of the wrapper 20 may be described as extending along a "Y" axis, and the width may be described as extending along an "X" axis. The depth of the wrapper 20 may be described as extending along a "Z" axis. The X, Y, and Z axes as used herein are each perpendicular to the others; e.g. if the X and Y axes are used to define a plane, the Z axis is perpendicular to the X-Y plane, etc. The front panel 22 has an interior surface 36 and an exterior surface 38. The back panel 24 has an interior surface 40 and an exterior surface 42.

Figure 2:
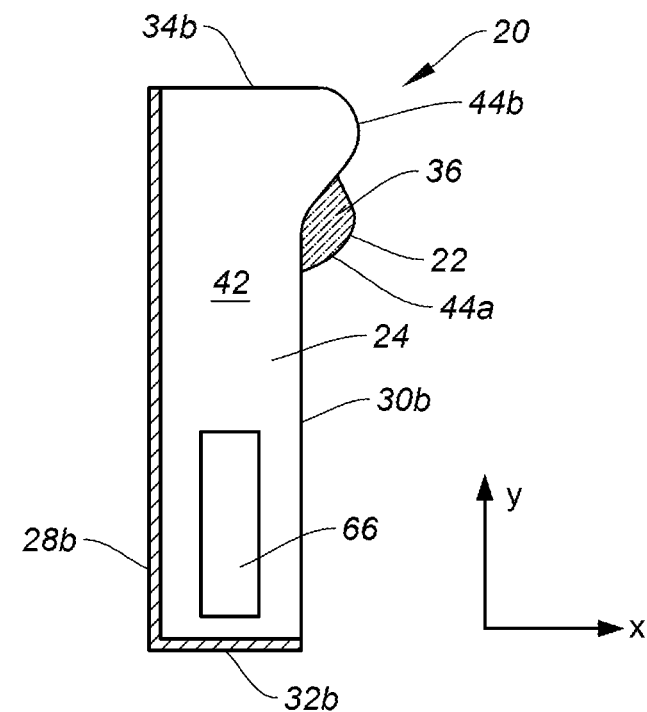
FIG. 2 is a diagrammatic planar view of the present wrapper (back panel side) in a new product configuration.

In some embodiments, the wrapper 20 may include one or more tabs (or the like) attached to (or integrally formed with) the front and back panels 22, 24 to facilitate opening of the wrapper 20. For example, as can be seen in FIGS. 1 and 2, in some embodiments the front panel 22 may include a tab 44a (e.g., integrally formed with the front panel 22) that extends widthwise outwardly from the open side lengthwise edge 30a, extending lengthwise a distance along the edge, and the back panel 24 may include a tab 44b (e.g., integrally formed with the front panel 22) that extends widthwise outwardly from the open side lengthwise edge 30b, extending lengthwise a distance along the edge. The present disclosure is not limited to the aforesaid tab embodiments; e.g., tabs may be affixed to the exterior surfaces 38, 42 of the respective panels 22, 24, etc. The tabs 44a, 44b may be configured in a variety of different shapes; e.g., shapes that can be easily grasped between a user's digits, tabs that have a desirable aesthetic shape, combinations thereof, etc.

In some embodiments, the front panel tab 44a and the back panel tab 44b may be partially misaligned from one another along the respective lengthwise edges. As can be seen in FIGS. 1 and 2, in those embodiments wherein the front panel tab 44a is misaligned with the back panel tab 44b, a portion of the interior surface 40 of the back panel tab 44b can be seen in the front panel planar view, and a portion of the interior surface 36 of the front panel tab 44a can be seen in the back panel planar view. As a result of the lengthwise misalignment, each tab 44a, 44b can be easily recognized and grasped by the user.

In some embodiments, the interior surfaces 36, 40 of the front panel 22 and back panel 24 may have a feature (e.g. a color, aesthetic feature, print pattern, surface texture etc.) different from that of the exterior surfaces 38, 42 of the respective front panels 22, 24. As a result, the tabs 44a, 44b may have a sensory cue (e.g., visual cue, tactile cue, etc.) that makes each tab readily distinguishable from the other, making it easier for the user to recognize the tabs 44a, 44b when opening the wrapper 20. In further embodiments, the tabs 44a and 44b match the rest of their respective front panels 22 and 24 to maintain an entirely uniform external wrapper 20. The present disclosure is not limited to misaligned tabs, or any particular sensory cue.

In further embodiments, the interior surface 60 of the wrapper 20 may have a sensory cue (e.g., visual cue, tactile cue, etc. . . . ) that is different from the front panel 22 and back panel 24. The difference in cue from the interior surface 60 of the wrapper 20 and the exterior surface 23 having front and back panels 22 and 24, respectively, can provide a deviation in how the consumer perceives her interaction with the product. For instance, the front panel 22 and back panel 24 may have an aesthetic that provides a discreet appearance, while the interior surface 60 provides a contrasting aesthetic that elicits an invigorating, surprising and/or enthusiastic perception of the user. In some embodiments, the exterior surface 23 has an aesthetic that provides a discreet appearance, while the interior surface 60 provides a contrasting aesthetic that elicits an invigorating, surprising and/or enthusiastic perception of the user. The discreetness of the initial appearance of the wrapper 20 (i.e., prior to being opened), is further enhanced by the wrapper 20 obfuscating the feminine hygiene product such as tampon 21. In some embodiments, the exterior surface 23 is at least substantially opaque, or has an aesthetic that masks the appearance of the feminine hygiene product such as tampon 21.

In the embodiment shown in FIGS. 1 and 2, the front panel tab 44a has the same shape as the back panel tab 44b, although the two tabs are misaligned with one another. In alternative embodiments, the front and back panel tabs 44a, 44b may have respectively different shapes. Embodiments of the present wrapper 20 may include tabs that differ in shape from one another, and that are misaligned.

Figure 6:
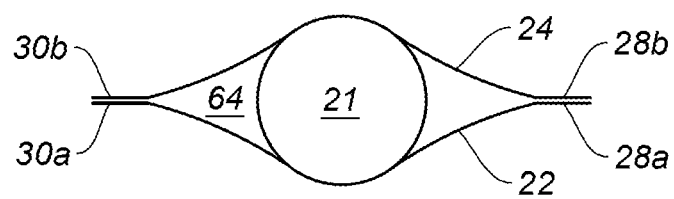
FIG. 6 is a diagrammatic view of the present wrapper as shown in FIG. 1, sectioned at line 6-6.
Figure 7:
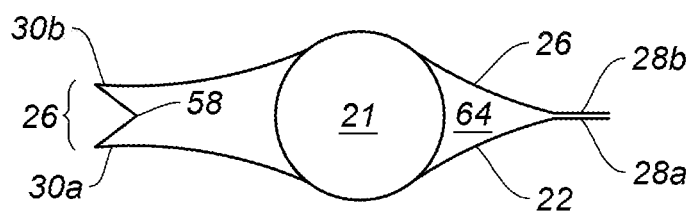
FIG. 7 is a diagrammatic view of the present wrapper as shown FIG. 6, with the expandable side panel slightly spread to illustrate the expandable side panel.

In some embodiments (e.g. see FIG. 5), the expandable side panel 26 is defined by a lengthwise extending first side edge 46, a lengthwise extending second side edge 48, a top edge 50, and a bottom edge 52. The expandable side panel 26 has an interior surface 54 and an exterior surface 56. The expandable side panel 26 includes a feature that allows the expandable side panel 26 to assume a closed configuration wherein the surface area of the expandable side panel 26 assumed between front and back panels 22, 24 is minimal (e.g. the configuration assumed when the wrapper 20 is in the new product configuration) and also an expanded configuration wherein the surface area of the expandable side panel 26 assumed between front and back panels 22, 24 is maximal (e.g. the configuration assumed when the wrapper 20 is in the open configuration). An example of the aforesaid feature is one or more lengthwise extending folds 58 (referred to hereinafter as "pleats") disposed between the first and second lengthwise extending side edges 46, 48 of the expandable side panel 26. FIGS. 5-12 illustrate non-limiting examples of such pleats 58. Specifically, the embodiments in FIGS. 5 and 8-12 include two pleats 58, each pleat 58 having a bend axis 60 and each pleat 58 connected to the other pleat along a bend axis 62. The present disclosure is not limited to this particular example and may have fewer or more pleats (e.g. FIG. 7 illustrate an expandable side panel 26 that has a single pleat), or may have some other fold configuration. Moreover the expandable side panel 26 is not limited to any particular shape; e.g. the expandable side panel 26 may have a diamond, rectangular, oval, triangular, or polyhedron shape, or any combination thereof.

The interior surface 60 defines interior cavity 60 of the wrapper 20. The interior surfaces 36, 40, 54 of the front panel 22, the back panel 24, and the expandable side panel 26 define an interior cavity 64 of the wrapper 20.

Figure 3:
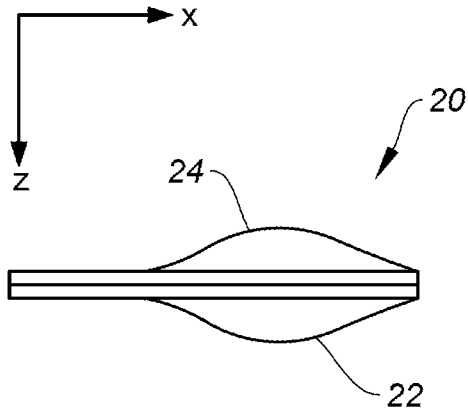
FIG. 3 is a diagrammatic top view of the present wrapper in a new product configuration.
Figure 4:
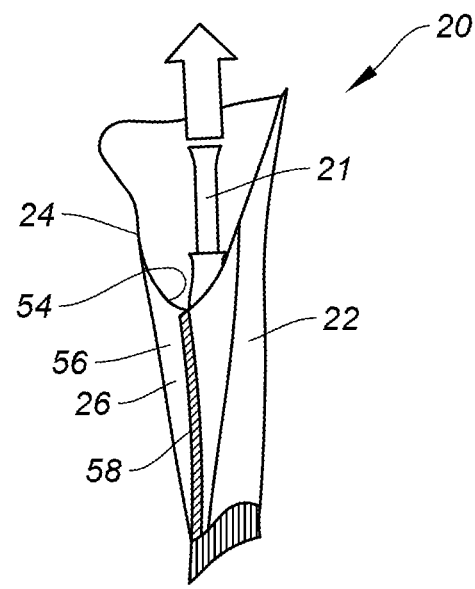
FIG. 4 is a diagrammatic perspective view of the present wrapper in an open configuration.
Figure 5:
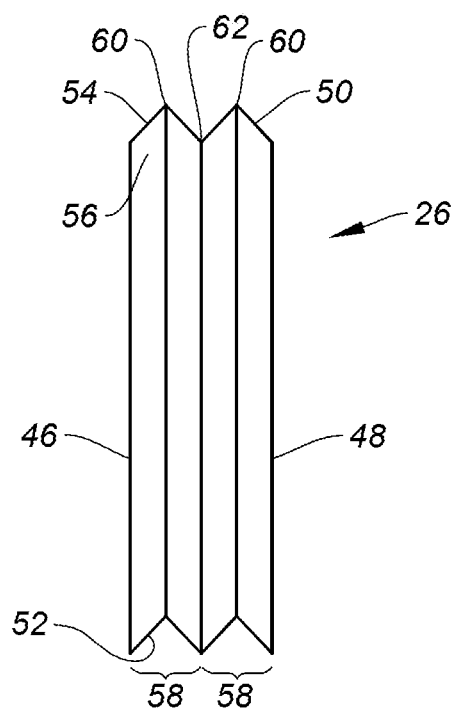
FIG. 5 is a diagrammatic sectional view proximate the top edge of the expandable side panel.

In the new product configuration of the embodiments shown in FIGS. 1-3, the closed side lengthwise edges 28a, 28b of the front and back panels 22, 24 are attached to one another along the length of the wrapper 20, and the bottom widthwise edges 32a, 32b of the front and back panels 22, 24 are attached to one another along the width of the wrapper 20. Preferably, the front and back panels 22, 24 are attached to one another along the closed side lengthwise edges 28a, 28b and the bottom widthwise edges 32a, 32b in a manner that creates a closed seam to prevent materials entering or exiting the interior cavity 64 of the wrapper 20. In these embodiments, the closed side lengthwise edge and bottom widthwise edge seams are not intended to be opened during normal use of the wrapper 20 as will be described below. In other embodiments, lengthwise edges 28a and 28b may be integrally formed such that front panel 22 and back panel 24 are a unitary piece thereby having, a unitary exterior surface 23 and interior surface 60. In FIGS. 1 and 2, the panels 22, 24 are diagrammatically depicted as having bonded seams along the aforesaid edges, but the present wrapper 20 is not limited thereto.

In the new product configuration of the embodiments shown in FIGS. 1 and 2, the expandable side panel 26 is folded in a manner that the side panel 26 is disposed between the front panel 22 and the back panel 24 along the open side lengthwise edges 30a, 30b; i.e. in a front planar view of the wrapper 20 in the new product configuration, the expandable side panel 26 cannot be seen. This folding configuration is preferable as it reduces the initial size of the wrapper 20 and thereby helps maintain the wrapper in a discreet state prior to use. To illustrate, FIG. 6 shows a sectional view of the wrapper 20 (section taken at line 6-6 of FIG. 1. In the new product configuration, wherein the open side lengthwise edges 30a, 30b of the front and back panels 22, 24 are in close proximity to one another. FIG. 7 shows another sectional top view of the wrapper 20, wherein the open side lengthwise edges 30a, 30b of the front and back panels 22, 24 are slightly separated from one another to illustrate the expandable feature (e.g. folds) of the expandable side panel 26.

In the new product configuration, a portion or all the open side lengthwise edges 30a, 30b of the front and back panels 22, 24 may be attached to one another in a manner that the attached portion(s) can be selectively detached from one another to allow access to the interior cavity 64 of the wrapper 20. Similarly, a portion of or all the top widthwise edges of the front and back panels 22, 24 may be attached to one another in a manner that the attached portion(s) can be selectively detached from one another to allow access to the interior cavity 64 of the wrapper 20. Examples of bow the aforesaid edges may be attached to one another include a continuous seam along the respective edge and a line of weakness disposed adjacent the edge. The line of weakness provides a mechanism where the seam may be torn apart and the seam thereby opened. In another example, the aforesaid edges may be adhered to one another using an adhesive, or via tape, VELCRO, etc. The present wrapper 20 is no limited to any particular attachment mechanism.

Figure 8:
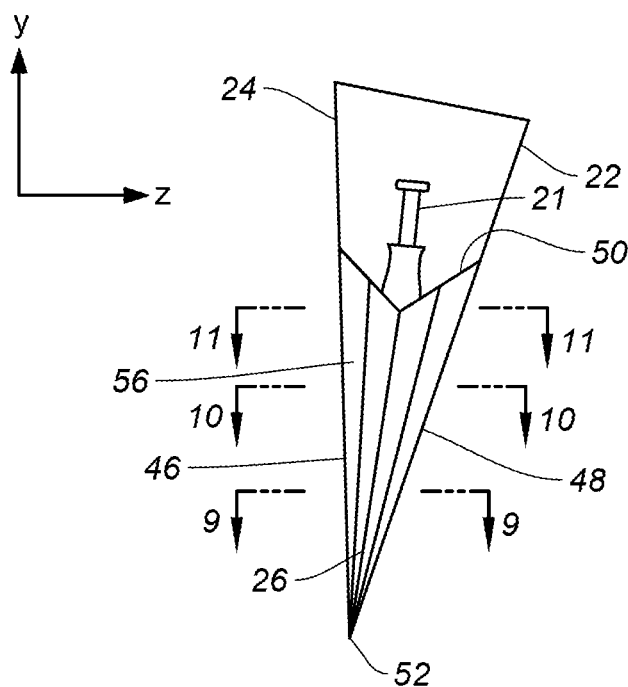
FIG. 8 is a side view illustrating an expandable side panel embodiment with a V-shaped top edge.
Figures 9, 10:
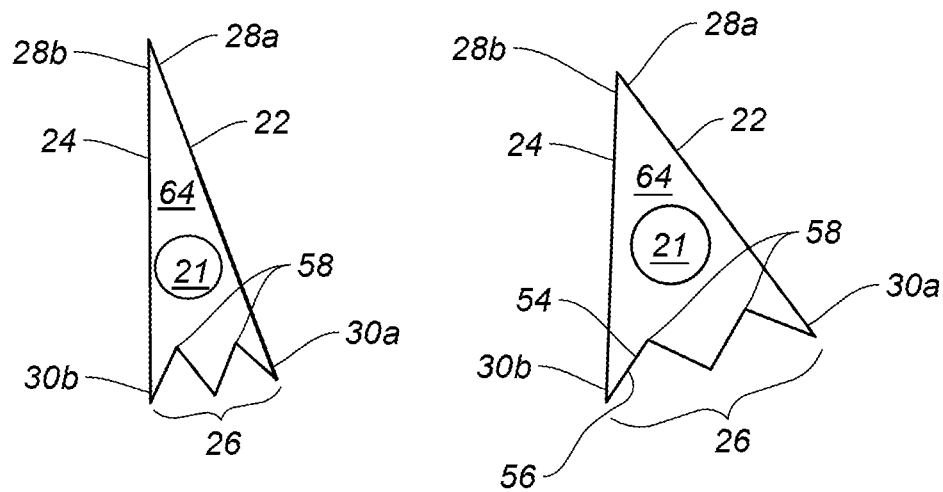
FIG. 9 is a diagrammatic sectional view of the present wrapper in an open configuration proximate the bottom edge of the wrapper, at line 9-9 of FIG. 8.
FIG. 10 is a diagrammatic sectional view of the present wrapper in an open configuration proximate the bottom edge of the wrapper, at line 10-10 of FIG. 8.

FIGS. 8-12 illustrate the above-described wrapper 20 embodiments in an open configuration. FIG. 8 is a side view illustrating an expandable side panel 26 embodiment with a V-shaped top edge. FIG. 9 is a diagrammatic sectional view proximate the bottom edge of the expandable side panel 26 (e.g. a section view taken at line 9-9 of FIG. 8). FIG. 11 is a diagrammatic sectional view proximate the top edge of the expandable side panel 26 (e.g., a section view taken at line 11-11 of FIG. 8). FIG. 10 is a sectional view taken at position between the sections shown in FIGS. 9 and 11 (e.g. a section view taken at line 10-10 of FIG. 8). FIG. 12 illustrates the expandable side panel 26 extended outwardly. It should be noted that the wrapper 20 is shown diagrammatically in FIGS. 8-12. Preferred embodiments of the present wrapper 20 are made of a thin, flexible polymeric material. The flexible material facilitates disposing the wrapper 20 into the open configuration and the sharp corners shown in FIGS. 8-12 (shown to facilitate the present description) are typically more rounded, less sharp (e.g., see FIGS. which characteristic typically facilitates a maximum sized opening into the interior cavity 64 of the wrapper 20.

The expandable side panel 26 of the present wrapper 20 provides an opening into the interior cavity 64 of the wrapper 20 that is substantially greater than the interior cavity opening of many prior art wrappers. Furthermore, the expandable side panel 26 of the present wrapper 20 substantially increases the volume of the interior cavity 64 of the wrapper 20 when the present wrapper 20 is in the open configuration. The substantial interior cavity opening (and interior cavity 64 volume) of the present wrapper 20 greatly facilitates the removal of a new product from the interior cavity 64 of the present wrapper 20 and the insertion of a used product into the interior cavity 64 of the present wrapper 20. In the open configuration, the interior cavity 64 of the present wrapper 20 may increase by as much as 80% of the wrapper 20 in its new product configuration.

Advantages of the present wrapper 20 are clear when one considers existing prior art wrappers. For example, some prior art wrappers are substantially cylindrical. Access to the interior cavity of the prior art wrapper (to permit removal of the unused product) is achieved by tearing the wrapper across its width. In these instances, the opening to the interior cavity is the diameter of the cylindrical wrapper, which diameter is typically not significantly larger than the diameter of the product itself. Once the unused product is removed, the user is tasked with opening the limited diameter of the wrapper, and then inserting a used product back into the limited diameter opening. In many instances, the prior art wrapper may not have a means to seal the used product within the wrapper. The expandable side panel 26 of the present wrapper 20 overcomes the aforesaid shortcomings by providing an opening into the interior cavity 64 of the wrapper 20 that is substantially greater than the interior cavity opening of many prior art wrappers. In one embodiment, the user detaches the front panel 22 from the back panel 24 via tabs 44a and 44b, and the expandable side panel 26 opens-up to enable the consumer to easily remove the tampon 21. The wrapper 20, courtesy of the expandable side panel 26, stays in an expanded open state during removal of the tampon 21 and optionally for insertion of a soiled product thereafter. In further embodiments, the expandable side panel provides [as it relates to the wrapper 20, (e.g., front panel 22 and back panel 24), in an initial, prior-to-use, un-expanded state] an expanded volume, and/or an increased surface area along inner surface 60 for easier insertion of a soiled product for disposal. In yet further embodiments, after the wrapper 20 has received a soiled product, the expandable side panel 26 can be collapsed and/or folded to provide a volume and/or surface area that is less than in a fully-expanded state, thereby providing further discreet disposal. The wrapper 20 shown in FIGS. 13A-13D diagrammatically illustrates the present wrapper 20, starting with the new product configuration (FIG. 13A) on the left, and then the progressively to the right, the wrapper 20 in the open configuration (FIG. 13B), then the product being removed (FIG. 13C), and then finally the wrapper 20 in a closed configuration with a used product disposed in the interior cavity 64 of the wrapper 20 (FIG. 13D). As can be seen, in the new product configuration (as well as the closed configuration) the outer dimensions of the present wrapper 20 are such that the wrapper 20 is a discreet package, but in the open configuration there is substantial access into the interior cavity 64 of the wrapper 20.

As indicated above, in some embodiments the present wrapper 20 may also be configured in closed used product configuration and a folded used product configuration. Once the wrapper 20 has been opened and the new product removed, it may be desirable to store the used applicator and/or a used product (e.g. a tampon) within the now empty wrapper 20. In some embodiments of the present wrapper 20, the present wrapper 20 may include a re-attachment mechanism (e.g., adhesive, tape, VELCRO, etc.) along a portion or all of the open side lengthwise edges 30a, 30b of the front and back panels 22, 24, so that the aforesaid edges (or a portion thereof) can be selectively reattached to one another. Similarly, a portion or all of the top widthwise edges of the front and back panels 22, 24 may include a re-attachment mechanism (e.g., adhesive, tape, VELCRO, etc.) so that the aforesaid edges (or a portion thereof) can be selectively reattached to one another. Once the edges are selectively reattached to one another, the used product is safely contained within the wrapper 20 (now in the closed used product configuration) and can be disposed of discreetly.

Figure 14:
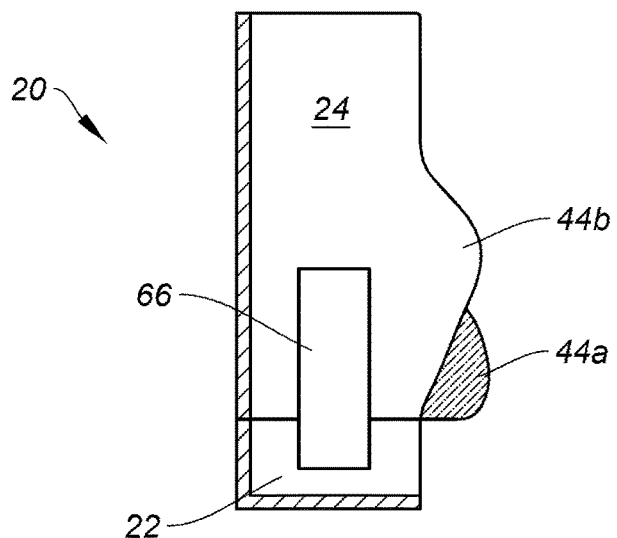
FIG. 14 is a diagrammatic planar view of the present wrapper in a folded used product configuration.

In some embodiments, the present wrapper 20 may be lengthwise folded into a folded used product configuration (e.g. see FIG. 14). In these embodiments, the present wrapper 20 may include a mechanism for maintaining the wrapper 20 in a lengthwise folded form. For example, a length of resealable tape 66 may be attached to an outside surface of one of the front or back panels 22, 24. The user may fold the present wrapper 20 lengthwise; e.g. folding the wrapper 20 to bring the top edges 34a, 34b of the panels 22, 24 toward the bottom edges 32a, 32b, and the resealable tape 66 can be used to hold the wrapper 20 in the folded configuration. Alternatively, a layer of adhesive may be applied to a portion of an outside surface of one of the front or back panels 22, 24, which adhesive may be covered by a releasable coversheet. Prior to folding the wrapper 20, the coversheet is removed, and the folded portion of the wrapper 20 is rotated into contact with the layer of adhesive which maintains the wrapper 20 in the folded configuration thereafter. The present wrapper 20 may include both reattachment mechanism along one or both edges, and a mechanism for maintaining the wrapper 20 in a lengthwise folded form. In the folded configuration, the size of wrapper 20 may be decreased considerably (up to 80% decrease) to enable discretion during disposal of used product.

The present wrapper 20 can be made from a variety of different materials and is not limited to any particular material. The front panel 22, back panel 24, and expandable side panel 26 may be made of the same or different materials. In a preferred embodiment, the front, rear and side panels 22, 24, 26 are a single panel that is cut and folded into the configurations described above. In these instances, the bottom widthwise edge and the closed lengthwise edge can be sealed to form the interior cavity 64. Acceptable wrapper 20 materials include polymeric films (PE, PP, and PET), cellophane, polyamide, elastic material, nonwovens, foil, paper, laminates (film to film, film to nonwoven, etc.) and fabrics. Polymeric films are particularly useful because the bottom widthwise and the closed lengthwise edges can be thermally bonded and thereby sealed.

Figure 15:
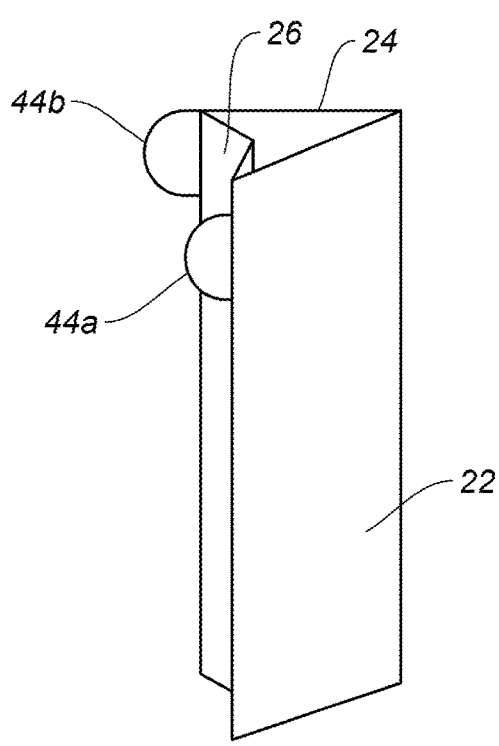
FIG. 15 is a diagrammatic view of an embodiment of the present wrapper.
Figure 16:
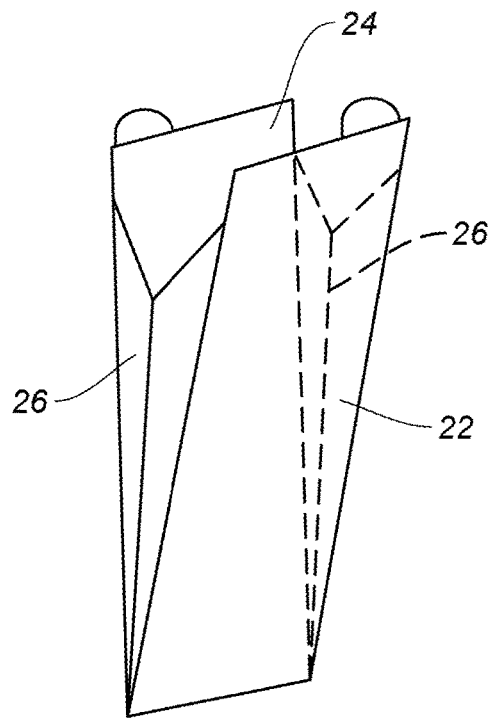
FIG. 16 is a diagrammatic view of an embodiment of the present wrapper.

Embodiments of the present wrapper 20 have been described above as having a single expandable side panel 26 that is fixed between the front and back panel 24 at the bottom widthwise edge. In the open configuration of these embodiments, the expandable side panel 26 can be opened to assume a substantially V-shaped configuration. The present wrapper 20 is not limited to these embodiments. For example, in an alternative embodiment (see FIG. 15), the wrapper 20 may have a single expandable side panel 26 that is not fixed between the front and back panel 24 at the bottom widthwise edges 32a, 32b, but rather the expandable side panel 26 may expand along the entire open lengthwise edges 30a, 30b; i.e. the side panel 26 may assume a rectangular shape when the wrapper 20 is in the open configuration with a bottom panel that extends between the front, back, and expandable side edges. A further embodiment (see FIG. 16) may include an expandable side panel 26 on each lengthwise side 28a, 28b, 30a, 30b of the front and back panels 22, 24. In both of these embodiments, adhesive or the like could be used to maintain the expandable side panel 26 folded while the wrapper 20 is in the new product configuration.

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one of ordinary skill in the art will appreciate that the steps described in conjunction with the illustrative figures may be performed in other than the recited order, and that one or more steps illustrated may be optional in accordance with aspects of the disclosure. One or more features described in connection with a first embodiment may be combined with one or more features of one or more additional embodiments.

The invention claimed is:

1. A feminine hygiene product wrapper, comprising:
a panel having a pair of lengthwise edges, a bottom widthwise edge, a top widthwise edge, an interior surface and an exterior surface; and
an expandable side panel that extends between the lengthwise edges of the panel, which the expandable side panel has an interior surface, an exterior surface, and a top widthwise edge;
wherein the wrapper is closed along the bottom widthwise edge of the panel,
wherein the interior surface of the panel and the expandable side panel form an interior cavity operable to hold a feminine hygiene product;
wherein the expandable side panel extends along less than an entire side length of the feminine hygiene product wrapper;
wherein in a new product configuration, the expandable side panel has a pleat that is folded such that the expandable side panel is disposed between the panel lengthwise edges that are attached to each other; and
wherein the wrapper is selectively configurable in the new product configuration wherein the interior cavity is closed adjacent the top widthwise edge of the panel, and an open configuration wherein the expandable side panel is at least partially expanded and the interior cavity of the wrapper is open,
wherein in the open configuration, the interior cavity is open at the top widthwise edge of the panel and at least partially down the panel lengthwise edges above the expandable side panel.

2. The feminine hygiene product wrapper of claim 1, wherein the wrapper further comprises a pair of tabs that extend outwardly from either the top widthwise edge of the panel or the pair of lengthwise edges of the panel.

3. The feminine hygiene product wrapper of claim 2, wherein the pair of tabs are misaligned.

4. The feminine hygiene product wrapper of claim 1, wherein the interior surface has an interior sensory cue that is distinct from and contrasts with an exterior surface cue on the exterior surface.

5. The feminine hygiene product wrapper of claim 4, wherein the exterior sensory cue is discrete.

6. The feminine hygiene product wrapper of claim 1, wherein in the open configuration the interior cavity is up to about 80% larger than the interior cavity in the new product configuration.

7. A feminine hygiene product wrapper having a feminine hygiene product, comprising:
a front panel having a closed side lengthwise edge, an open side lengthwise edge, a bottom widthwise edge, and a top widthwise edge;
a back panel having a closed side lengthwise edge, an open side lengthwise edge, a bottom widthwise edge, and a top widthwise edge; and
an expandable side panel having a lengthwise extending first side edge, a lengthwise extending second side edge, a top edge, and a bottom edge, wherein the lengthwise extending first side edge is attached to the open side lengthwise edge of the front panel, and the lengthwise extending second side edge is attached to the open side lengthwise edge of the back panel;
wherein the expandable side panel extends along less than an entire side length of the feminine hygiene product wrapper;
wherein in a new product configuration, the feminine hygiene product is contained within an interior cavity of the feminine hygiene wrapper between the back panel and the front panel, and
wherein in the new product configuration, the expandable side panel has a pleat that is folded such that the expandable side panel is disposed in the interior cavity between the front panel and the back panel;
wherein in an open configuration, the interior cavity is open at the top widthwise edges of the front panel and the back panel and at least partially down the open side lengthwise edges of the front panel and the back panel above the expandable side panel.

8. The feminine hygiene product wrapper of claim 7, wherein the wrapper further comprises a pair of tabs that extend outwardly from either the top widthwise edges or the open side lengthwise edges of the front panel and the back panel.

9. The feminine hygiene product wrapper of claim 8, wherein the pair of tabs are misaligned.

10. The feminine hygiene product wrapper of claim 8, wherein one tab of the pair of tabs extends from the back panel and wherein the other tab of the pair of tabs extends from the front panel.

11. The feminine hygiene product wrapper of claim 7, wherein an interior surface of the wrapper has an interior sensory cue that is distinct from and contrasts with an exterior surface cue on an exterior surface of the wrapper.

12. The feminine hygiene product wrapper of claim 11, wherein the exterior sensory cue is discreet.

13. The feminine hygiene product wrapper of claim 7, wherein in the open configuration the interior cavity is up to about 80% larger than the interior cavity in the new product configuration.

\* \* \* \* \*